United States Patent
Chung et al.

(10) Patent No.: US 11,805,971 B2
(45) Date of Patent: Nov. 7, 2023

(54) METHOD AND APPARATUS FOR DIAGNOSING URINARY DISTURBANCES BY SIMULTANEOUSLY MEASURING URINARY FLOW RATE AND RESIDUAL URINE

(71) Applicant: INDUSTRY-ACADEMIC COOPERATION FOUNDATION, YONSEI UNIVERSITY, Seoul (KR)

(72) Inventors: Byung Ha Chung, Seoul (KR); Kwang Suk Lee, Seoul (KR); Kyo Chul Koo, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 246 days.

(21) Appl. No.: 17/387,382

(22) Filed: Jul. 28, 2021

(65) Prior Publication Data
US 2021/0353248 A1 Nov. 18, 2021

Related U.S. Application Data

(63) Continuation of application No. PCT/KR2020/000993, filed on Jan. 21, 2020.

(30) Foreign Application Priority Data

Jan. 29, 2019 (KR) .................. 10-2019-0010882

(51) Int. Cl.
 *A61B 8/08* (2006.01)
 *G01F 9/00* (2006.01)
(52) U.S. Cl.
 CPC . *A61B 8/08* (2013.01); *G01F 9/00* (2013.01)

(58) Field of Classification Search
 CPC .......... A61B 8/08; A61B 5/103; A61B 5/107; A61B 5/1073; G01F 9/00
 See application file for complete search history.

(56) References Cited

U.S. PATENT DOCUMENTS

| 2006/0111633 | A1  | 5/2006 | McMorrow et al. |
| 2009/0030326 | A1* | 1/2009 | Kim ............... A61B 5/1075 |
|              |     |        | 600/459 |

(Continued)

FOREIGN PATENT DOCUMENTS

| KR | 1020020074589 A | 10/2002 |
| KR | 1020070074288   | 7/2007  |

(Continued)

OTHER PUBLICATIONS

International Search Report for International Application No. PCT/KR2020/000993, dated May 28, 2020, 13 pages.

(Continued)

*Primary Examiner* — Chao Sheng
(74) *Attorney, Agent, or Firm* — Burris Law, PLLC

(57) ABSTRACT

The present disclosure relates to a method and apparatus for diagnosing urinary disturbances by simultaneously measuring a urinary flow rate and residual urine. The method for diagnosing urinary disturbances according to the present disclosure includes obtaining at least one ultrasonic image of a bladder for each unit time from a patient who is urinating, obtaining at least one urine region image for each unit time from the at least one ultrasonic image for each unit time, calculating at least one estimated urine volume for each unit time based on an area of the at least one urine region image for each unit time, calculating at least one parameter value with respect to urinary disturbances based on the at least one estimated urine volume for each unit time, and outputting the at least one parameter value.

9 Claims, 14 Drawing Sheets

(56) References Cited

U.S. PATENT DOCUMENTS

| | | | |
|---|---|---|---|
| 2016/0058411 A1* | 3/2016 | Yoshimura | A61B 8/54 600/438 |
| 2016/0259994 A1 | 9/2016 | Ravindran et al. | |
| 2017/0055874 A1* | 3/2017 | Papirov | A61B 5/07 |
| 2017/0258386 A1 | 9/2017 | Woltjer et al. | |
| 2018/0284250 A1 | 10/2018 | Bjaerum | |

FOREIGN PATENT DOCUMENTS

| | | | |
|---|---|---|---|
| KR | 1020070105097 A | 10/2007 | |
| KR | 100779548 | 11/2007 | |
| KR | 1020100116262 | 11/2010 | |
| KR | 1020170066322 A | 6/2017 | |
| KR | 1020180071947 A | 6/2018 | |
| KR | 101874613 B1 | 7/2018 | |
| KR | 101930883 | 12/2018 | |

OTHER PUBLICATIONS

Notice of Preliminary Rejection issued in KR Application No. 10-2021-0010882, dated Jul. 27, 2021, and English Translation, 14 pages.

Notice of Final Rejection issued in KR Application No. 10-2021-0010882, dated Jan. 4, 2022, and English Translation 6 pages.

Notice of Allowance issued in corresponding KR Application No. 10-2019-0010882, dated Jan. 18, 2022, and English Translation 7 pages.

* cited by examiner

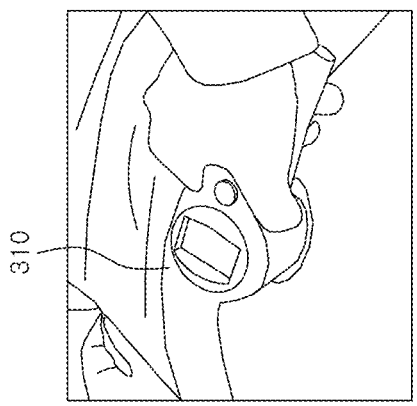
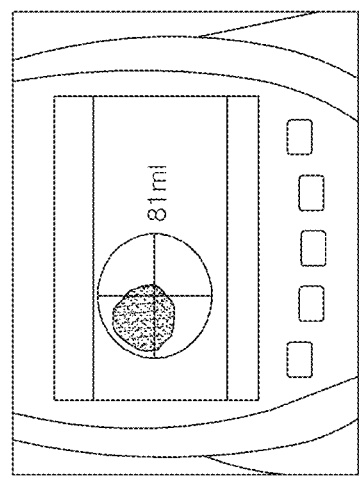
FIG.3

METHOD AND APPARATUS FOR DIAGNOSING URINARY DISTURBANCES BY SIMULTANEOUSLY MEASURING URINARY FLOW RATE AND RESIDUAL URINE

CROSS-REFERENCE TO RELATED APPLICATIONS

This application is a continuation of International Application No. PCT/KR2020/000993, filed on Jan. 21, 2020, which claims priority to and the benefit of Korean Application No. 10-2019-0010882, filed on Jan. 29, 2019. The disclosures of the above applications are incorporated herein by reference.

FIELD

The present disclosure relates to a method and apparatus for diagnosing urinary disturbances and, more specifically, to a method and apparatus for diagnosing urinary disturbance by simultaneously measuring a urinary flow rate and residual urine.

BACKGROUND

The statements in this section merely provide background information related to the present disclosure and may not constitute prior art.

A bladder is a hollow sac-like muscular organ responsible for storage and excretion of urine and is located in the middle of a human pelvis. In a patient with urinary disturbances, it is known that a thickness of a muscular layer of a bladder is correlated with a volume of the bladder and severity of voiding symptoms. Although effectiveness of ultrasound examination for the bladder has been proven, clinicians have limited use of the bladder ultrasound examination for the diagnosis of urinary disturbances in consideration of a cost versus a diagnostic benefit of the bladder ultrasound examination.

Objective tests for the urinary disturbances are divided into uroflowmetry and bladder sono scan. In a case of the uroflowmetry, an amount of urine discharged from the bladder is checked in real time so that the urinary flow rate and a change in the urinary flow rate are checked. Failure to urinate in a limited collection container will result in inaccuracy of the test. In particular, in the case of men, they complain that they cannot urinate as usual due to a structural problem of a test device. In addition, in a case of the bladder sono scan, when a clinician measures the residual urine, a patient should lie on the bed, and the patient feels shame because the anatomical location of the bladder is in the pelvis.

Therefore, there is a need for a method and apparatus that can increase the accuracy of the examination for the urinary disturbances and reduce the patient's shame by unifying the uroflowmetry and the bladder sono scan using ultrasound.

SUMMARY

This section provides a general summary of the disclosure and is not a comprehensive disclosure of its full scope or all of its features.

The present disclosure provides a method and apparatus that can simultaneously perform the uroflowmetry and bladder sono scan by using machine learning to quickly calculate a volume and a change in the volume of a three-dimensional urine region in a bladder from a two-dimensional ultrasonic image of the bladder obtained for each unit time while a patient is urinating.

The present disclosure has the following objects so as to solve the above problems.

The present disclosure is directed to providing a method and apparatus capable of increasing accuracy of a test for urinary disturbances and reducing a patient's shame by unifying uroflowmetry and bladder sono scan using ultrasound.

The present disclosure is directed to providing a method and apparatus capable of simultaneously performing the uroflowmetry and bladder sono scan by using machine learning to quickly calculate a volume and a change in the volume of a three-dimensional urine region in a bladder from a two-dimensional ultrasonic image of the bladder obtained for each unit time while a patient is urinating.

The problems to be solved of the present disclosure are not limited to those described above, and other problems not described will be clearly understood by those of ordinary skill in the art from the following description.

One aspect of the present disclosure provides a method for diagnosing urinary disturbances, the method including obtaining at least one ultrasonic image of a bladder for each unit time from a patient who is urinating, obtaining at least one urine region image for each unit time from the at least one ultrasonic image for each unit time, calculating at least one estimated urine volume for each unit time based on an area of the at least one urine region image for each unit time, calculating at least one parameter value with respect to urinary disturbances based on the at least one estimated urine volume for each unit time, and outputting the at least one parameter value.

Another aspect of the present disclosure provides an apparatus for diagnosing urinary disturbances, the apparatus including an input device configured to obtain at least one ultrasonic image for each unit time for a bladder from a patient who is urinating, a memory configured to store the at least one ultrasonic image for each unit time, an output device, and a processor, in which the processor obtains the at least one urine region image for each unit time from the at least one ultrasonic image for each unit time, calculates at least one estimated urine volume for each unit time based on an area of the at least one urine region image for each unit time, calculates at least one parameter value with respect to urinary disturbances based on the at least one estimated urine volume for each unit time, and outputs the at least one parameter value.

Still another aspect of the present disclosure provides a computer program configured to execute the method for diagnosing urinary disturbances and stored in a computer-readable storage medium.

According to the present disclosure, it is possible to provide a method and apparatus that can increase accuracy of a test for urinary disturbances and reduce a patient's shame by unifying uroflowmetry and bladder sono scan using ultrasound.

According to the present disclosure, it is possible to provide a method and apparatus that can simultaneously perform the uroflowmetry and bladder sono scan by using machine learning to quickly calculate a volume and a change in the volume of a three-dimensional urine region in a bladder from a two-dimensional ultrasonic image of the bladder obtained for each unit time while a patient is urinating.

Effects of the present disclosure are not limited to those described above, and other effects not described will be clearly understood by those of ordinary skill in the art from the following description.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which:

FIG. 3 illustrates an example of bladder sono scan for a patient with urinary disturbances;

FIGS. 6A to 6C illustrate changes in a bladder, a detrusor muscle, and a urine region during urination, wherein FIG. 6A shows a bladder is filled with urine and is inflated, FIG. 6B shows the bladder contracts as the urine begins to be discharged from the bladder, and FIG. 6C shows the bladder contracts further as more urine is discharged from the bladder;

Figure 2:
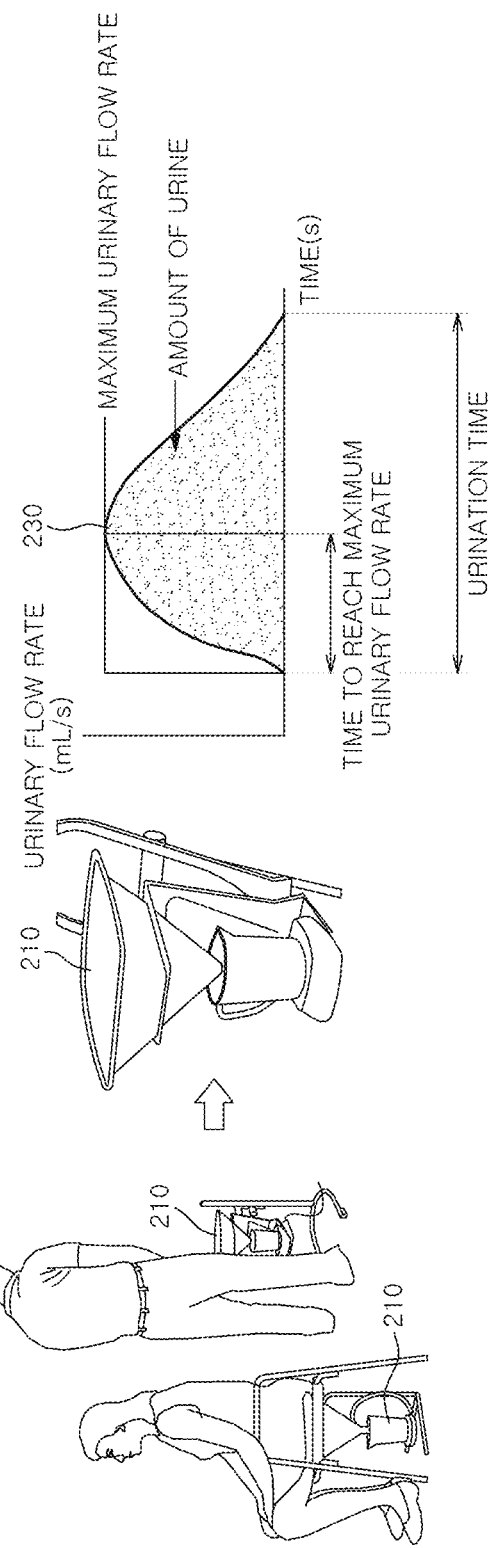
FIG. 2 illustrates an example of uroflowmetry for a patient with urinary disturbances.
Figure 7A:
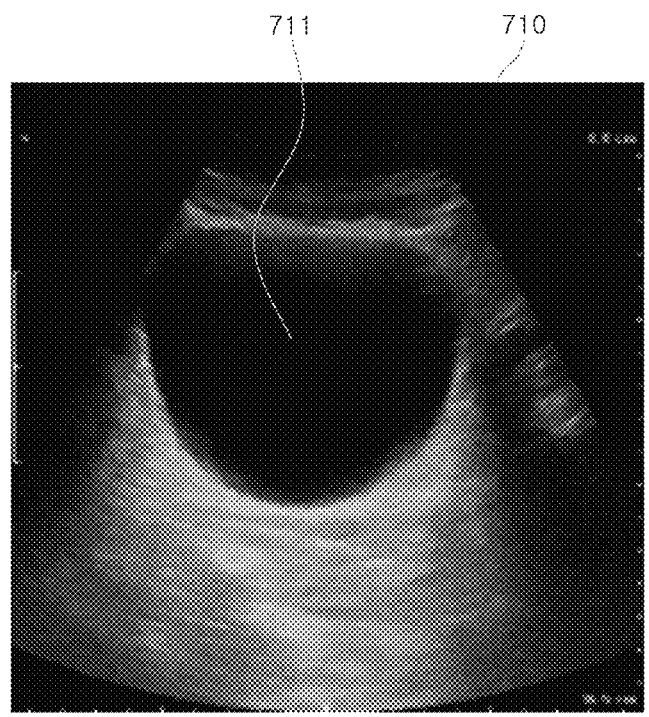
Figure 7B:
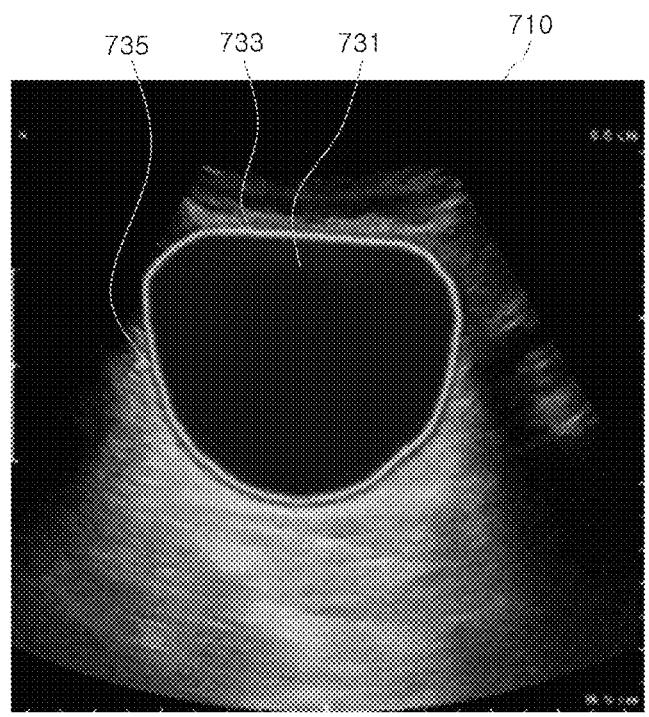
Figure 8:
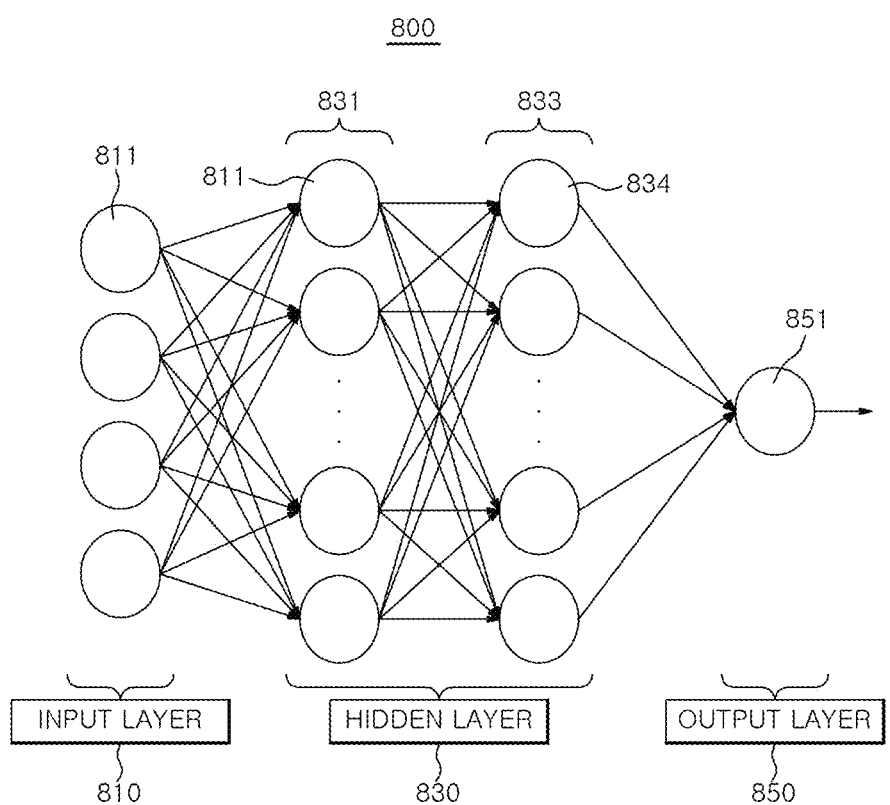
Figure 9:
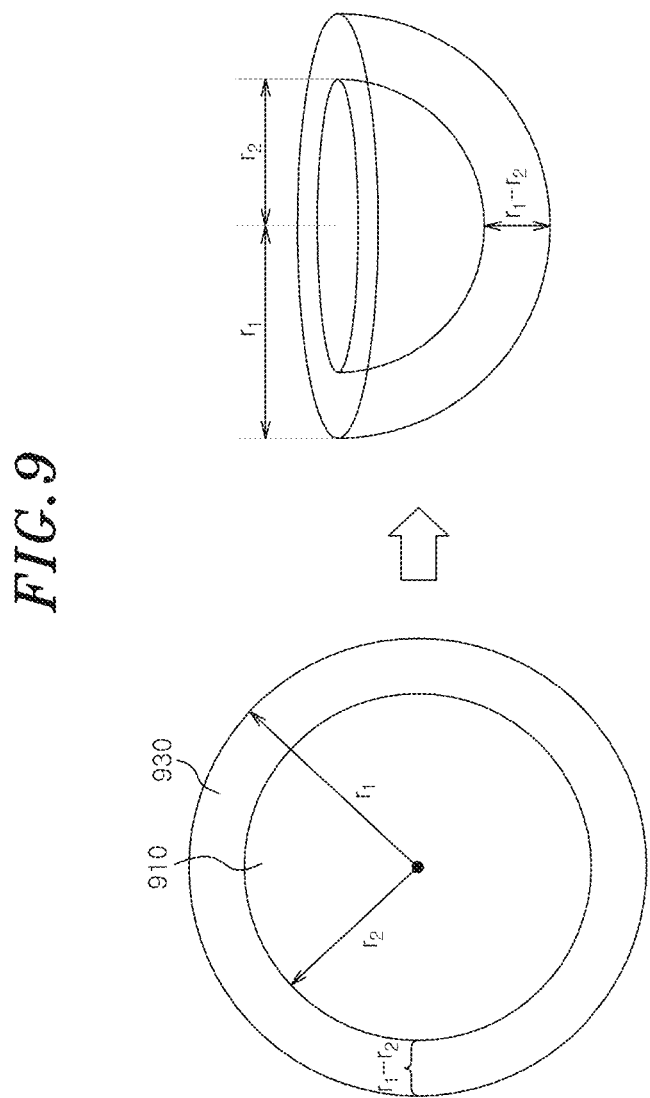
Figure 10:
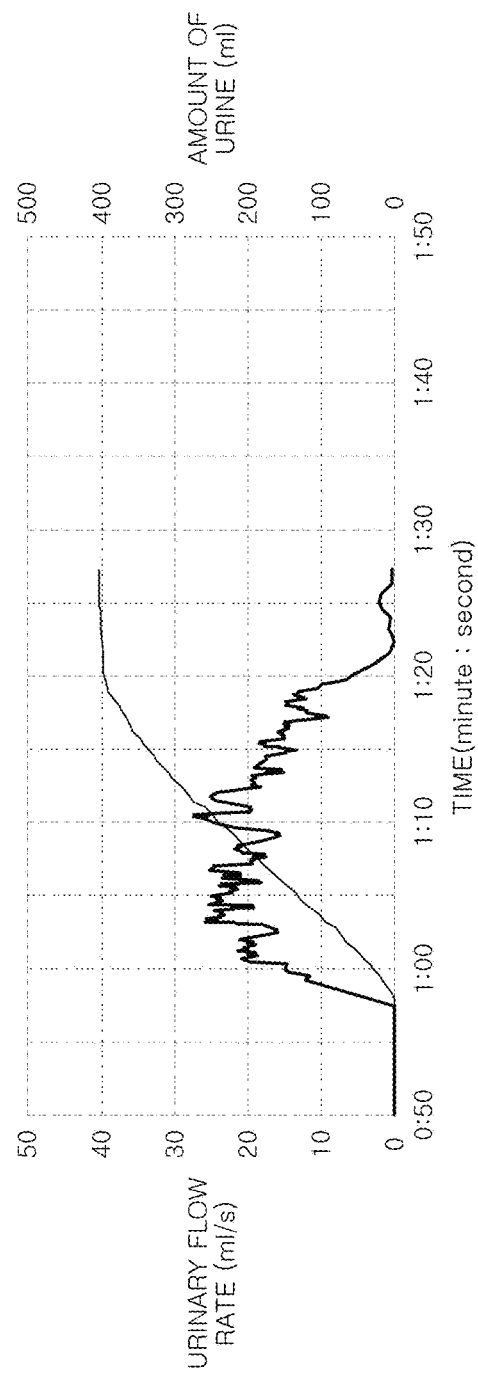
Figure 11:
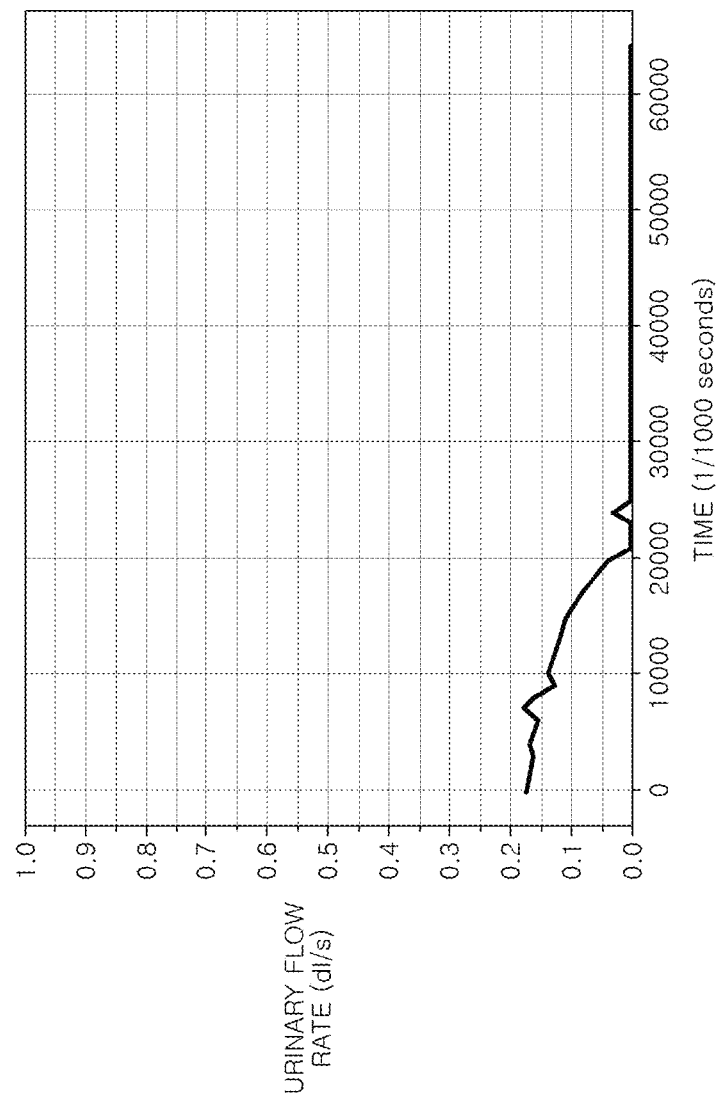

FIGS. 7A and 7B illustrate an example of a process of separating an outer wall region, a detrusor muscle region, and a urine region of a bladder from an ultrasonic image obtained from a patient who is urinating according to various embodiments of the present disclosure, wherein FIG. 7A shows an ultrasonic image of the bladder captured in real time during urination, and FIG. 7B shows an ultrasonic image of the bladder in which a layer of the detrusor muscle in the bladder and the outer wall of the bladder are separated;

FIG. 8 illustrates a structure of a multi-layer perceptron (MLP) for generating a machine learning-based urine region separation model according to various embodiments of the present disclosure;

FIG. 9 illustrates a process of calculating a three-dimensional urine volume from a two-dimensional ultrasonic image according to various embodiments of the present disclosure;

FIG. 10 illustrates a graph of a urinary flow rate and an amount of urine measured by a method for diagnosing urinary disturbances according to various embodiments of the present disclosure; and FIG. 11 illustrates a graph of a urinary flow rate measured by the method of the uroflowmetry of FIG. 2.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Hereinafter, embodiments of the present disclosure will be described with reference to the accompanying drawings in detail so that those of ordinary skill in the art to which the present disclosure pertains can easily implement them. The present disclosure may be embodied in several different forms and is not limited to the embodiments described herein.

Figure 1:
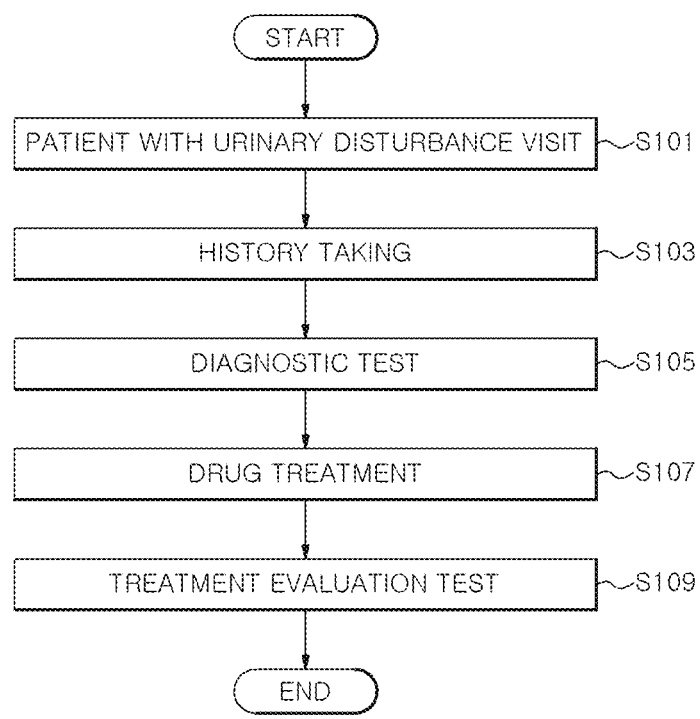
FIG. 1 illustrates an example of an algorithm for diagnosis and treatment of a patient with urinary disturbances.

FIG. 1 illustrates an example of an algorithm for diagnosis and treatment of a patient with urinary disturbances.

Urinary disturbances (dysuria) are a comprehensive term for abnormalities that may occur during a urination process. The urinary disturbances are common diseases encountered by the general public when there are abnormalities in bladder, prostate, and urethra. Representative diseases of the urinary disturbances include benign prostatic hyperplasia in men, stress incontinence in women, and neurogenic bladder that can appear in any gender and age. Recently, as the social structure of Korea is aging, about 50% of male patients complain of urinary disturbances due to the benign prostatic hyperplasia. In addition, a prevalence of overactive bladder was found in about 12.2% of the population, and this is also related to the aging of the Korean social structure.

Referring to FIG. 1, in Step S101, for patients visiting with urinary disturbances, a clinician classifies severity of the urinary disturbances through history taking, examination, or the like through Steps S103 and below.

In Step S103, the clinician, through the history taking, checks a previous surgical history, possibilities of urethral stricture and urea damage, indolent hematuria that may suspect bladder cancer or the like, urgency suggesting neurogenic bladder, and the like.

In Step S105, the clinician performs uroflowmetry for a urinary flow rate (UFR) through an international prostate symptom score (IPSS) and an overactive bladder symptom score (OABSS) and bladder sono scan through bladder scan for a residual urine volume (RV). For male patients, the clinician may perform additional tests such as prostate specific antigen (PSA), transrectal ultrasound (TRUS), and rectal examination.

In Step S107, the clinician classifies a patient diagnosed with urinary disturbances according to the diagnostic test result in Step S105 according to the severity of the urinary disturbances and recommends drug treatment as the primary treatment. The clinician uses an alpha blocker, such as anti-cholinergics, 5-alpha-reductase inhibitor (5-ARI), or the like, in consideration of the patient's symptoms and checks a treatment response through the questionnaires, uroflowmetry, and bladder sono scan.

In Step S109, the clinician performs a treatment evaluation test through a urination symptom questionnaire, treatment evaluation according to drugs or treatment methods, and treatment evaluation according to surgical methods in order to observe progress every 3, 6, 9, and 12 months.

The present disclosure provides a method and apparatus for unifying the uroflowmetry and bladder sono scan in Step S105.

FIG. 2 illustrates an example of uroflowmetry for a patient with urinary disturbances.

FIG. 3 illustrates an example of bladder sono scan for a patient with urinary disturbances.

Specifically, FIGS. 2 and 3 illustrate two objective tests for diagnosing urinary disturbances.

Objective tests for urinary disturbances are divided into the uroflowmetry and bladder sono scan.

Referring to FIG. 2, in the uroflowmetry, a patient urinates in the collection container 210, a urinary flow rate 230 and a change in the urinary flow rate are measured by checking the flow rate in the collection container 210 in real time, and thus, a plurality of factor values for urination are collected. A uroflowmetry allows the clinician to determine how well the patient's bladder and sphincter are functioning. The plurality of factor values that can be obtained through the uroflowmetry include a maximum urinary flow rate, a total urination time, a time to reach the maximum urinary flow rate, and an amount of urine.

The clinician can determine the presence of obstructions in a urinary tract from whether the graph of urinary flow rate has a normal shape. The clinician can determine from average and maximum values of the urinary flow rates whether the urinary tract is blocked or how serious the obstruction in the urinary tract is. In addition, the result of uroflowmetry can be used to identify other urinary diseases such as benign prostatic hyperplasia.

However, the uroflowmetry has a structural problem that may cause inaccuracy of the test. Since the uroflowmetry has a structure in which the urination is performed in the limited collection container, there is a possibility that not all of the urine is collected in the collection container during the urination. In particular, male patients often complain that they cannot urinate as usual due to structural problems with the test device.

Referring to FIG. 3, the bladder sono scan is for measuring the residual urine volume (RV) in the bladder by performing bladder scan using ultrasound. Specifically, the bladder sono scan is for measuring a volume of urine in black shades after sweeping the bladder in the shape of a brisket using the ultrasonic scanning device 310. In the case of bladder sono scan, when the clinician measures residual urine, the patient should lie on a bed, an anatomical position of the bladder is in the pelvis, and thus, there is a problem that the patients feel shame.

The bladder is a hollow sac-like muscular organ responsible for storage and excretion of urine and is located in the middle of the human pelvis. In a patient with urinary disturbances, it is known that a thickness of a muscular layer of a bladder is correlated with a volume of the bladder and severity of voiding symptoms. Although ultrasound examination for the bladder has been proven effective, clinicians have limited use of the bladder ultrasound examination for the diagnosis of urinary disturbances in consideration of a cost versus a diagnostic benefit of the bladder ultrasound examination.

Therefore, there is a need for a method and apparatus that can increase the accuracy of the examination for urinary disturbances and reduce the patient's shame by unifying the uroflowmetry and the bladder sono scan using ultrasound.

Figure 4:
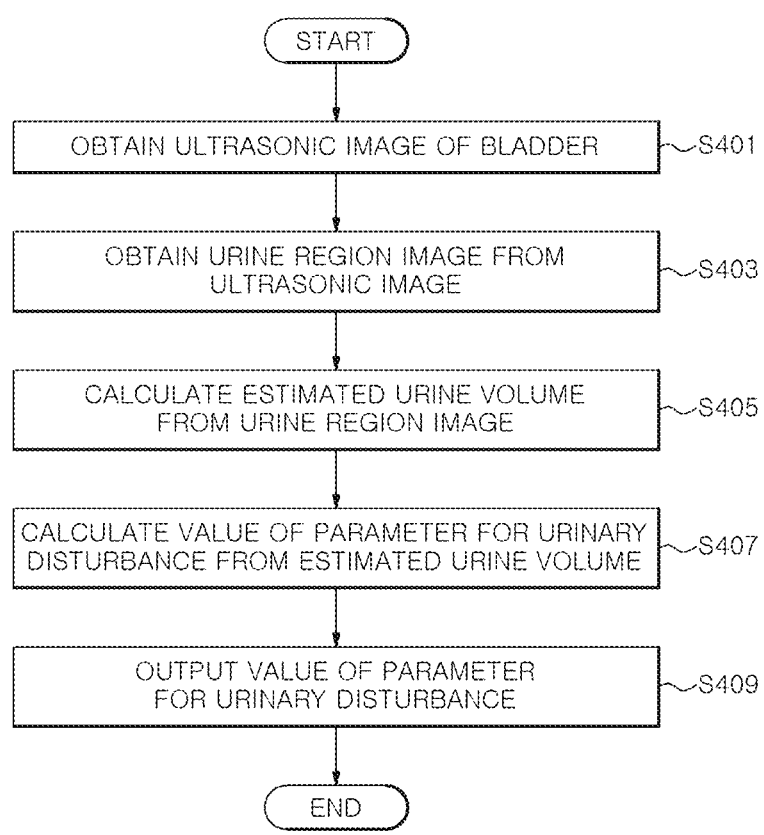
FIG. 4 illustrates an example of a method for diagnosing urinary disturbances according to various embodiments of the present disclosure.

FIG. 4 illustrates an example of a method for diagnosing the urinary disturbances according to various embodiments of the present disclosure.

In Step S401, at least one ultrasonic image of the bladder for each unit time is obtained from the patient who is urinating. Specifically, in Step S401, at least one ultrasonic image of the bladder for each unit time of the patient who is urinating is obtained from an ultrasonic image device included inside an apparatus for diagnosing urinary disturbances or connected to the outside of the apparatus.

The unit time may be set according to the number of frames per second (fps) set in the ultrasonic imaging device. For example, when the number of fps of the ultrasonic image device is set to 60 fps, 60 ultrasonic images per second can be obtained for the bladder in the process of performing the urination. That is, in this case, the unit time for obtaining the ultrasonic image is 1/60 seconds. The unit time may be adaptively adjusted in consideration of the patient's typical urination time and the total number of frames of the ultrasonic image device. That is, when the total number of frames is fixed, a shorter unit time may be set by setting a higher fps for a patient with a short urination time. In addition, a longer unit time may be set by setting a lower fps for a patient with a long normal urination time.

The ultrasonic imaging device should be fixedly positioned at the patient's lower abdomen while the patient is urinating in order to obtain a real-time ultrasonic image of the bladder of the patient who is urinating. According to one embodiment, the ultrasonic imaging device may be fixed to the patient's lower abdomen using a belt, and the patient may urinate in a state where the patient wears the belt-type ultrasonic imaging device.

Obtaining the real-time ultrasonic image in the urination process for the patient who is urinating may fundamentally block structural inaccuracies due to the patient's urination posture when compared to the uroflowmetry in FIG. 2.

In addition, since the ultrasonic image is obtained while the patient urinates as usual, it is possible to solve the problem of the patient lying in bed and feeling shame about the clinician when compared to the bladder sono scan of FIG. 3.

In Step S403, at least one urine region image for each unit time is obtained from the at least one ultrasonic image for each unit time.

The urine region is shaded in black in the ultrasonic image. Therefore, the urine region image may be obtained through red-green-blue (RGB) analysis of each pixel of the ultrasonic image.

According to various embodiments of the present disclosure, a step of obtaining the least one urine region image for each unit time may include a step of separating an outer wall region, a detrusor muscle region, and a urine region of the bladder from the at least one ultrasonic image for each unit time, and a step of obtaining the at least one urine region image for each unit time as the urine region. The outer wall region of the bladder refers to an outer border of a black shaded portion in the ultrasonic image of the bladder. The detrusor muscle region refers to a gray region between a completely black urine region and the outer wall region among the black shaded portions. The urine region refers to the completely black portion among the black shaded portions in the ultrasonic image of the bladder.

According to one embodiment, the outer wall region of the bladder means a region of an edge where a difference in RGB values between adjacent pixels is higher than a predetermined threshold value. That is, the difference between the RGB value of an inner region and the RGB value of an outer region with the outer wall region of the bladder as a boundary is higher than the predetermined threshold value. Since the RGB value of the inner region with the outer wall region of the bladder as a boundary is relatively close to the RGB value of the black compared to the RGB value of the outer region, the outer wall region may be referred to as the black shaded portion.

According to one embodiment, the detrusor muscle region refers to a region formed by pixels having the RGB value higher than the predetermined threshold value among the pixels in the black shaded portion, that is, a region formed by pixels not close to the RGB value of the black.

According to one embodiment, the urine region means a region formed by pixels having the RGB value lower than the predetermined threshold value among the pixels in the black shaded portion, that is, a region formed by pixels close to the RGB value of the black. Since the RGB value of the urine region is relatively close to the RGB value of the black in the inner region of the outer wall of the bladder that is relatively black in the ultrasonic image compared to the RGB value of regions other than the urine region, the urine region may be referred to as a completely black portion.

According to various embodiments of the present disclosure, the urine region image may be analyzed from the ultrasonic image using machine learning. In addition, according to various embodiments of the present disclosure, it is possible to separate the outer wall region of the bladder, the detrusor muscle region, and the urine region from the ultrasonic image using the machine learning.

When performing the analysis of the urine region image using the machine learning, the step of obtaining the at least one urine region image for each unit time is performed using a urine region separation model stored in a memory.

According to various embodiments of the present disclosure, the urine region separation model includes an input layer, a plurality of hidden layers, and an output layer. Here, the step of obtaining the least one urine region image for each unit time may include a step of inputting the RGB value of each pixel in the at least one ultrasonic image for each unit time to the input layer, a step of connecting units defined as a plurality of nodes stored in each of the plurality of hidden layers to the RGB value of each pixel in the at least one ultrasonic image for each unit time, a step of generating an estimated value for the urine region whether or not the urine region is present in each pixel in the at least one ultrasonic image for each unit time based on a correlation between the RGB value of each pixel in the at least one ultrasonic image for each unit time and the units, and a step of obtaining the at least one urine region image for each unit time as each pixel in the at least one ultrasonic image for each unit time when the estimated value is equal to or more than the predetermined threshold value.

According to various embodiments of the present disclosure, the units are formed by combining the RGB values of each pixel in the at least one ultrasonic image for each unit time, and the output layer includes a true unit that is a unit having an estimation result in which each pixel in the at least one ultrasonic image for each unit time is the urine region and a false unit that is a unit having an estimation result in which each pixel in the at least one ultrasonic image for each unit time is not the urine region. Here, the step of generating the estimated value for the urine region whether or not the urine region is present in each pixel in the at least one ultrasonic image for each unit time based on the correlation between the RGB value of each pixel in the at least one ultrasonic image for each unit time and the units includes a step of applying a weight having a positive value to a connection with the true unit and a weight having a negative value to a connection with the false unit when it is estimated that each pixel in the at least one ultrasonic image for each unit time in any one of the units is highly likely to be the urine region, a step of applying the weight having the negative value to the connection with the true unit and the weight having the positive value to the connection with the false unit when it is estimated that each pixel in the at least one ultrasonic image for each unit time in any one of the units is unlikely to be the urine region, and a step of generating an estimated value indicating that each pixel in the at least one ultrasonic image for each unit time is the urine region when a total of connections between the units and the true unit is positive or greater than a preset value.

In the same way as above, the outer wall region, detrusor muscle region, and urine region of each bladder may be separated from the ultrasonic image using the machine learning.

In Step S405, the at least one estimated urine volume for each unit time is calculated based on the area of the at least one urine region image for each unit time.

Since the bladder increases or decreases in volume like a water balloon according to the amount of urine, the volume thereof may be calculated by assuming the bladder to be one sphere. Since the urine region does not have a shape of a perfect circle, the estimated urine volume may be calculated by calculating a radius of a circle having the same area as the urine region and then calculating a volume of a sphere having the calculated radius. Through this method, a three-dimensional estimated urine volume may be calculated from a two-dimensional ultrasonic image.

According to various embodiments of the present disclosure, the step of calculating the at least one estimated urine volume for each unit time includes a step of calculating a radius of a circle having the same area as an area of the at least one urine region image for each unit time, and calculating the at least one estimated urine volume for each unit time as a volume of a sphere having the radius.

In Step S407, a value of at least one parameter for urinary disturbances is calculated based on at least one estimated urine volume for each unit time.

According to various embodiments of the present disclosure, the at least one parameter includes at least one of the urinary flow rate for each unit time, a time taken to empty the bladder, the amount of urine, and a residual urine volume. Here, the urinary flow rate for each unit time is a change amount for each unit time of the at least one estimated urine volume for each unit time. That is, the urinary flow rate for each unit time is a differential value for unit time of the at least one estimated urine volume for each unit time. The time taken to empty the bladder is a length of a time interval from a time when the least estimated urine volume for each unit time starts to change to a time when the change in the at least one estimated urine volume for each unit time stops. The value of the amount of urine is a difference between an estimated urine volume calculated at the time when the at least one estimated urine volume for each unit time starts to change and an estimated urine volume calculated at the time when the change in the at least one estimated urine volume for each unit time stops. The value of the amount of urine is also an integral value for each unit time of the urinary flow rate for each unit time. The value of the residual urine volume is a value of the estimated urine volume calculated at the time when the change in the at least one estimated urine volume for each unit time stops.

In Step S409, the value of the at least one parameter calculated in Step S407 is output. Specifically, in Step S409, the value of the at least one parameter calculated in Step S407 is output to another apparatus included in the apparatus for diagnosing the urinary disturbances or connected to the outside of the apparatus. Another apparatus included in the apparatus for diagnosing the urinary disturbances or connected to the outside of the apparatus may include a display device that visually displays the value of the at least one parameter calculated in Step S407, a wired/wireless communication device that transmits the value of the at least one parameter calculated in Step S407 to another terminal device connected by a wire or wirelessly connected through a network, a memory that stores the value of the at least one parameter calculated in Step S407, or the like.

Since the value of the at least one parameter calculated in Step S407 is a value corresponding to each time value one-to-one for each unit time during the urination, the value of the at least one parameter may be output in the form of a table in which a row or column is a time value for each unit time, or in the form of a graph in which an x-axis or a y-axis is a time value for each unit time.

A computer program according to various embodiments of the present disclosure is configured to perform the method for diagnosing the urinary disturbances according to various embodiments of the present disclosure and may be stored in a computer-readable storage medium.

Figure 5:
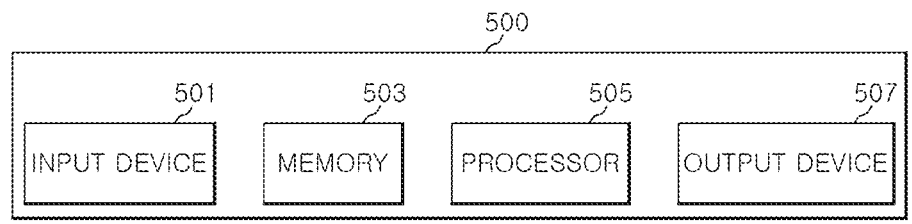
FIG. 5 illustrates an example of an apparatus for diagnosing urinary disturbances according to various embodiments of the present disclosure.

FIG. 5 illustrates an example of an apparatus for diagnosing the urinary disturbances according to various embodiments of the present disclosure.

Referring to FIG. 5, an apparatus 500 for diagnosing the urinary disturbances according to various embodiments of the present disclosure includes an input device 501, a memory 503, a processor 505, and an output device 507.

The input device 501 is connected to the processor 505 and inputs information or the like. According to one embodiment, the input device 501 may receive and input information from another device connected by a wire or wirelessly connected through a network.

According to one embodiment, the input device 501 is configured to obtain the at least one ultrasonic image, for each unit time, of the bladder from the patient who is urinating. Specifically, the input device 501 is configured to obtain the at least one ultrasonic image of the bladder, for each unit time, of the patient who is urinating from the ultrasonic image device included in the apparatus 500 for diagnosing the urinary disturbances or connected to the outside of the apparatus 500.

The unit time may be set according to the number of fps set in the ultrasonic imaging device. For example, when the number of fps of the ultrasonic image device is set to 60 fps, 60 ultrasonic images per second can be obtained for the bladder in the process of performing the urination. That is, in this case, the unit time for obtaining the ultrasonic image is 1/60 seconds. The unit time may be adaptively adjusted in consideration of the patient's typical urination time and the total number of frames of the ultrasonic image device. That is, when the total number of frames is fixed, a shorter unit time may be set by setting a higher fps for a patient with a short urination time. In addition, a longer unit time may be set by setting a lower fps for a patient with a long normal urination time.

The ultrasonic imaging device should be fixedly positioned on the patient's lower abdomen while the patient is urinating in order to obtain the real-time ultrasonic image of the patient's bladder who is urinating. According to one embodiment, the ultrasonic imaging device may be fixed to the patient's lower abdomen using a belt, and the patient may urinate in a state where the patient wears the belt-type ultrasonic imaging device.

Obtaining a real-time ultrasonic image in the urination process for a patient who is urinating may fundamentally block the structural inaccuracies due to the patient's urination posture when compared to the uroflowmetry in FIG. 2.

In addition, since the ultrasonic image is obtained while the patient urinates as usual, it is possible to solve the problem of the patient lying in bed and feeling shame about the clinician when compared to the bladder sono scan of FIG. 3.

The memory 503 is connected to the processor 505 and stores data such as a basic program, an application program, and setting information for an operation of the processor 505. The memory 503 may include a volatile memory, a non-volatile memory, or a combination of a volatile memory and a non-volatile memory. In addition, the memory 503 provides stored data according to a request of the processor 505. According to one embodiment, the memory 503 may be configured to store the at least one ultrasonic image for each unit time. According to one embodiment, the memory 503 may be configured to store the urine region separation model for separating the urine region image for each unit time from the at least one ultrasonic image for each unit time.

The processor 505 may be configured to implement procedures and/or methods proposed in the present disclosure. The processor 505 controls overall operations of the apparatus 500 for diagnosing the urinary disturbances. For example, the processor 505 inputs and outputs information and the like through the input device 501 and the output device 507. In addition, the processor 505 writes and reads data to and from the memory 503. The processor 505 may include at least one processor.

The processor 505 is configured to obtain the at least one urine region image for each unit time from the at least one ultrasonic image for each unit time, calculate at least one estimated urine volume for each unit time based on an area of the at least one urine region image for each unit time, calculate at least one parameter value with respect to the urinary disturbances based on the at least one estimated urine volume for each unit time, and output the at least one parameter value.

The urine region is shaded in black in the ultrasonic image. Therefore, a urine region image may be obtained through the RGB analysis of each pixel of the ultrasonic image.

According to various embodiments of the present disclosure, the processor 505 may be configured to separate the outer wall region, the detrusor muscle region, and the urine region of the bladder from the at least one ultrasonic image for each unit time and obtain the at least one urine region image for each unit time as the urine region.

The outer wall region of the bladder refers to the outer border of the dark shaded portion in the ultrasonic image of the bladder. According to one embodiment, the outer wall region of the bladder means the region of the edge where the difference in the RGB values between adjacent pixels is higher than a predetermined threshold value. That is, the difference between the RGB value of the inner region and the RGB value of the outer region with the outer wall region of the bladder as a boundary is higher than the predetermined threshold value. Since the RGB value of the inner region with the outer wall region of the bladder as a boundary is relatively close to the RGB value of the black color compared to the RGB value of the outer region, the outer wall region may be referred to as the black shaded portion.

The detrusor muscle region refers to the gray region between the completely black urine region and the outer wall region in the black shaded portion. According to one embodiment, the detrusor muscle region refers to the region formed by pixels having the RGB value higher than the predetermined threshold value among the pixels in the black shaded portion, that is, a region formed by pixels that are not close to (0, 0, 0) which is the RGB value of black.

The urine region refers to the completely black portion in the black shaded portion in the ultrasonic image of the bladder. According to one embodiment, the urine region means the region formed by the pixels having the RGB value lower than the predetermined threshold value among the pixels in the black shaded portion, that is, a region formed by the pixels close to the RGB value of black. Since the RGB value of the urine region is relatively close to the RGB value of black in the inner region of the outer wall of the bladder that is relatively black in the ultrasonic image compared to the RGB value of regions other than the urine region, the urine region may be referred to as the completely black portion.

According to various embodiments of the present disclosure, the processor 505 may be configured to analyze the urine region image from the ultrasonic image using the machine learning. In addition, according to various embodiments of the present disclosure, the processor 55 may separate the outer wall region, the detrusor muscle region, and the urine region of the bladder from the ultrasonic image using the machine learning.

The processor 505 may be configured to obtain at least one urine region image for each unit time using the urine region separation model stored in the memory when performing the analysis of the urine region image using the machine learning.

According to various embodiments of the present disclosure, the urine region separation model includes an input layer, a plurality of hidden layers and an output layer. Here, the processor 505 may be configured to input the RGB value of each pixel in the at least one ultrasonic image for each unit time to the input layer, connect the units defined as a plurality of nodes stored in each of the plurality of hidden layers to the RGB value of each pixel in the at least one ultrasonic image for each unit time, generate an estimated value for the urine region whether or not the urine region is present in each pixel in the at least one ultrasonic image for each unit time based on a correlation between the RGB value of each pixel in the at least one ultrasonic image for each unit time and the units, and obtain the at least one urine region image for each unit time as each pixel in the at least one ultrasonic image for each unit time when the estimated value is equal to or more than the predetermined threshold value.

According to various embodiments of the present disclosure, the units are formed by combining the RGB values of each pixel in the at least one ultrasonic image for each unit time, and the output layer includes the true unit that is the unit having the estimation result in which each pixel in the at least one ultrasonic image for each unit time is the urine region and the false unit that is the unit having the estimation result in which each pixel in the at least one ultrasonic image for each unit time is not the urine region. Here, the processor 505 may be configured to apply the weight having the positive value to the connection with the true unit and the weight having the negative value to the connection with the false unit when it is estimated that each pixel in the at least one ultrasonic image for each unit time in any one of the units is highly likely to be the urine region, apply the weight having the negative value to the connection with the true unit and the weight having the positive value to the connection with the false unit when it is estimated that each pixel in the at least one ultrasonic image for each unit time in any one of the units is unlikely to be the urine region, and generate the estimated value indicating that each pixel in the at least one ultrasonic image for each unit time is the urine region when a total of connections between the units and the true unit is positive or greater than a preset value.

In the same way as above, the processor 505 may be configured to separate the outer wall region, detrusor muscle region, and urine region of each bladder from the ultrasonic image using the machine learning.

Since the bladder increases or decreases in volume like a water balloon according to the amount of urine, the volume thereof may be calculated by assuming the bladder to be one sphere. Since the urine region does not have the shape of a perfect circle, the estimated urine volume may be calculated by calculating the radius of a circle having the same area as the urine region and then calculating the volume of a sphere having the calculated radius. Through this method, the processor 505 may be configured to calculate the three-dimensional estimated urine volume from the two-dimensional ultrasonic image.

According to various embodiments of the present disclosure, the processor 505 may be configured to calculate a radius of a circle having the same area as the area of the at least one urine region image for each unit time, and calculate the at least one estimated urine volume for each unit time as a volume of a sphere having the radius.

According to various embodiments of the present disclosure, the at least one parameter includes at least one of the urinary flow rate for each unit time, the time taken to empty the bladder, the amount of urine, and the residual urine volume. Here, the urinary flow rate for each unit time is the change amount for each unit time of the at least one estimated urine volume for each unit time. That is, the urinary flow rate for each unit time is a differential value for the unit time of the at least one estimated urine volume for each unit time. The time taken to empty the bladder is the length of the time interval from the time when the least estimated urine volume for each unit time starts to change to the time when the change in the at least one estimated urine volume for each unit time stops. The value of the amount of urine is a difference between the estimated urine volume calculated at the time when the at least one estimated urine volume for each unit time starts to change and the estimated urine volume calculated at the time when the change in the at least one estimated urine volume for each unit time stops. The value of the amount of urine is also an integral value for each unit time of the urinary flow rate for each unit time. The value of the residual urine volume is a value of the estimated urine volume calculated at the time when the change in the at least one estimated urine volume for each unit time stops.

The output device 507 is connected to the processor 505 and outputs information or the like. The output device 507 is configured to output a value of at least one parameter for urinary disturbances.

According to one embodiment, the output device 507 may be configured to output a value of at least one parameter for the urinary disturbances to another device included in the apparatus 500 for diagnosing the urinary disturbances or connected to the outside of the apparatus 500. Another device included in the apparatus 500 for diagnosing the urinary disturbances or connected to the outside of the apparatus 500 may include the display device that visually displays the value of the at least one parameter for the urinary disturbances, the wired/wireless communication device that transmits the value of the at least one parameter calculated to another terminal device connected by a wire or wirelessly connected through a network, the memory that stores the value of the at least one parameter for the urinary disturbances, or the like.

Since the value of the at least one parameter for the urinary disturbances is a value corresponding to each time value one-to-one for each unit time during the urination, the value of the at least one parameter may be output in the form of a table in which a row or column is a time value for each unit time, or in the form of a graph in which an x-axis or a y-axis is a time value for each unit time.

Figure 6A:
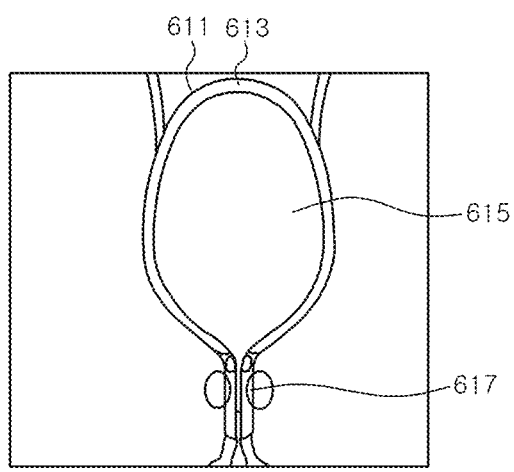
Figure 6B:
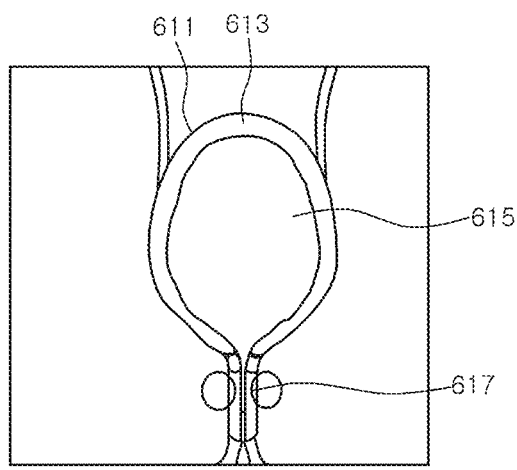
Figure 6C:
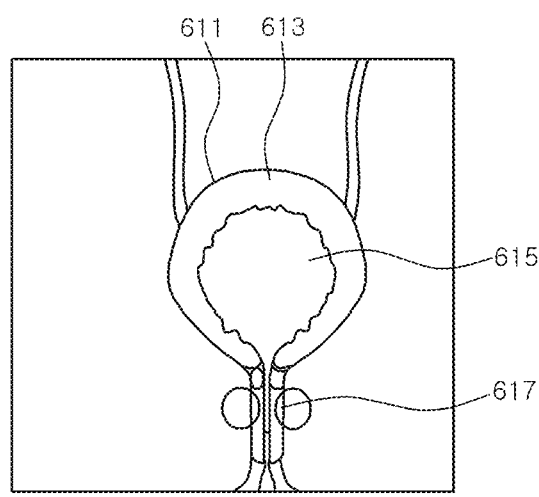

FIGS. 6A to 6C illustrate changes in the bladder, detrusor muscle, and urine region during urination. Specifically, FIGS. 6A to 6C illustrate a process in which urine sequentially exits from when the bladder is filled with the urine.

The present disclosure is based on two important facts. First, urine is discharged through contraction of the bladder, and a volume of the contracted bladder is equal to a volume of excreted urine. Considering a shape of a sac-like bladder, the ultrasonic image measured in two dimensions may be corrected in three dimensions, and through this correction, the volume of the bladder may be checked in real time. Second, a muscle layer of the bladder is thickened during contraction of the bladder. The muscle layer of the bladder is measured separately, and based on this, changes in the thickness of the muscle layer and the urine are recognized separately from the image.

Referring to FIG. 6A, a bladder 611 is filled with urine 615 in the bladder 611 while being inflated. In a process in which the bladder 611 is inflated, a detrusor muscle 613 relaxes, and a sphincter muscle 617 contracts.

Referring to FIG. 6B, the bladder 611 contracts and the urine 615 begins to be discharged from the bladder 611. During the contraction of the bladder 611, the detrusor muscle 613 contracts, and the sphincter muscle 617 relaxes. The contracted volume of the bladder 611 is equal to the volume of the discharged urine. In addition, as the bladder 611 contracts, the detrusor muscle 613 is gradually thickened.

Referring to FIG. 6C, as the bladder 611 contracts further, the urine 615 is discharged from the bladder 611 more. During the contraction of the bladder 611, the detrusor muscle 613 contracts, and the sphincter muscle 617 relaxes. The contracted volume of the bladder 611 is equal to the volume of the discharged urine. Moreover, as the bladder 611 contracts further, the detrusor muscle 613 becomes thicker.

Referring to FIGS. 6A to 6C, it can be seen that the volume of the discharged urine may be calculated based on the contracted volume of the bladder 611 during the urination process. In addition, since the thickness of the detrusor muscle 613 is not fixed and changes during the urination process, it can be seen that each thickness of the detrusor muscle 613 should be considered in each process of the urination.

FIGS. 7A to 7B illustrate an example of a process of separating the outer wall region, the detrusor muscle region, and the urine region of the bladder from the ultrasonic image obtained from a patient who is urinating according to various embodiments of the present disclosure.

In order to evaluate feasibility or industrial applicability of the present disclosure, from March 2017 to May 2017, an experiment was conducted with three patients complaining of the urinary disturbances and three patients in the normal group, who agreed to the uroflowmetry, the bladder sono scan, and capturing of real-time ultrasound image during urination.

In order to confirm the change in the volume of the bladder in real time, the ultrasonic image of the bladder was used as a deep learning technique during the machine learning to recognize the urine region in the bladder, the layer of the detrusor muscle in the bladder, and the outer wall of the bladder. For this, a recurrent neural network (RNN) technique was used.

Referring to FIGS. 7A and 7B, it was confirmed that an analysis method using the deep learning is effective in discriminating the urine region in the bladder, the layer of the detrusor muscle in the bladder, and the outer wall of the bladder from the ultrasonic image captured in real time during the urination.

Referring to FIG. 7A, a region 711 of the bladder may be visually confirmed in an ultrasonic image 710 of the bladder captured in real time during the urination.

Referring to FIG. 7B, it can be seen that a urine region 731 in the bladder, a layer 733 of the detrusor muscle in the bladder, and an outer wall 735 of the bladder may be separated from the ultrasonic image 710 of FIG. 7A using the deep learning.

When performing the analysis of the urine region image using the deep learning during the machine learning, the step of obtaining the at least one urine region image for each unit time is performed using the urine region separation model stored in the memory.

According to various embodiments of the present disclosure, the urine region separation model includes the input layer, the plurality of hidden layers, and the output layer. Here, a step of obtaining the urine region image in the bladder from the ultrasonic image captured in real time may include the step of inputting the RGB value of each pixel in the at least one ultrasonic image for each unit time to the input layer, the step of connecting units defined as the plurality of nodes stored in each of the plurality of hidden layers to the RGB value of each pixel in the at least one ultrasonic image for each unit time, the step of generating the estimated value for the urine region whether or not the urine region is present in each pixel in the at least one ultrasonic image for each unit time based on the correlation between the RGB value of each pixel in the at least one ultrasonic image for each unit time and the units, and the step of obtaining the at least one urine region image for each unit time as each pixel in the at least one ultrasonic image for each unit time when the estimated value is equal to or more than the predetermined threshold value.

According to various embodiments of the present disclosure, the units are formed by combining the RGB values of each pixel in the at least one ultrasonic image for each unit time, and the output layer includes the true unit that is a unit having the estimation result in which each pixel in the at least one ultrasonic image for each unit time is the urine region and the false unit that is a unit having the estimation result in which each pixel in the at least one ultrasonic image for each unit time is not the urine region. Here, the step of generating the estimated value for the urine region whether or not the urine region is present in each pixel in the at least one ultrasonic image for each unit time based on the correlation between the RGB value of each pixel in the at least one ultrasonic image for each unit time and the units includes the step of applying the weight having the positive value to the connection with the true unit and the weight having the negative value to the connection with the false unit when it is estimated that each pixel in the at least one ultrasonic image for each unit time in any one of the units is highly likely to be the urine region, the step of applying the weight having the negative value to the connection with the true unit and the weight having the positive value to the connection with the false unit when it is estimated that each pixel in the at least one ultrasonic image for each unit time in any one of the units is unlikely to be the urine region, and the step of generating an estimated value indicating that each pixel in the at least one ultrasonic image for each unit time is the urine region when a total of connections between the units and the true unit is positive or greater than a preset value.

In the same way as above, the outer wall region, detrusor muscle region, and urine region of each bladder may be separated from the ultrasonic image using the deep learning of the machine learning.

FIG. 8 illustrates a structure of a multi-layer perceptron (MLP) for generating a machine learning-based urine region separation model according to various embodiments of the present disclosure.

The deep learning is one of the emerging technologies in the field of machine learning recently and is a neural network that includes a plurality of hidden layers and a plurality of units included therein. When low level features are input to the deep learning model, the low level features are transformed into high level features that can better explain a problem to be estimated while passing through a plurality of hidden layers. In this process, since prior knowledge or intuition of an expert is not required, a subjective factor in feature extraction may be removed, and a model with higher generalization ability may be developed. Furthermore, in the case of the deep learning, since feature extraction and model construction are configured as one set, there is an advantage that a final model may be formed through a simpler process compared to the existing machine learning theories.

The MLP is a type of artificial neural network (ANN) with multiple nodes based on the deep learning. Each node uses a non-linear activation function with a neuron similar to an animal's connection pattern. This non-linear property makes it possible to linearly separate inseparable data.

Referring to FIG. 8, an artificial neural network 800 of the MLP model according to various embodiments of the present disclosure includes an input layer 810, a plurality of hidden layers 830, and an output layer 850.

Input data such as the RGB value of each pixel in at least one ultrasonic image for each unit time is input to the node of the input layer 810. Here, an RGB value 811 of each pixel in the at least one ultrasonic image for each unit time corresponds to the low level feature of the deep learning model.

In the node of the hidden layer 830, a calculation is performed based on the input factors. The hidden layer 830 is a layer in which units defined as a plurality of nodes formed by combining the RGB values 811 of each pixel in at least one ultrasonic image for each unit time are stored. The hidden layer 830 may include a plurality of hidden layers as illustrated in FIG. 8.

For example, when the hidden layer 830 includes a first hidden layer 831 and a second hidden layer 833, the first hidden layer 831 is a layer storing first units 832 defined as a plurality of nodes formed by combining the RGB values 811 of each pixel in the at least one ultrasonic image for each unit time, which is the lowest feature, and each of the first units 832 corresponds to an upper feature of the RGB value 811 of each pixel in the at least one ultrasonic image for each unit time. The second hidden layer 833 is a layer in which second units 834 defined as a plurality of nodes formed by combining the first units of the first hidden layer 831 are stored, and each of the second units 834 corresponds to an upper feature of the first unit 832.

The node of the output layer 850 indicates a calculated estimation result. A plurality of estimation result units 851 may be provided in the output layer 85. Specifically, the plurality of estimation result units 851 may include two units, that is, a true unit and a false unit. Specifically, the true unit is an estimation result unit in which each pixel in at least one ultrasonic image for each unit time is the urine region, and a false unit an estimation result unit in which each pixel in at least one ultrasonic image for each unit time is not the urine region.

Weights are applied to connections between the second units 834 and the estimation result units 851 included in the second hidden layer 833, which is the last layer among the hidden layers 830. Based on these weights, it is estimated whether each pixel in at least one ultrasonic image for each unit time is the urine region.

For example, when any one unit of the second units 834 estimates that each pixel in the at least one ultrasonic image for each unit time is the urine region, the unit is connected to each of the true unit and the false unit, the weight having the positive value is applied to the connection with the true unit, and the weight having the negative value is applied to the connection with the false unit. Conversely, when any one unit of the second units 834 estimates that each pixel in the at least one ultrasonic image for each unit time is not the urine region, the unit is connected to each of the true unit and the false unit, the weight having the negative value is applied to the connection with the true unit, and the weight having the positive value is applied to the connection with the false unit.

A plurality of connecting lines are formed between the plurality of second units 834 and the true unit. When the total sum of the plurality of connecting lines has a positive value, the RGB value 811 of each pixel in the at least one ultrasonic image for each unit time in the input layer 810 is estimated as factors of the urine region. According to one embodiment, whether each pixel in the at least one ultrasonic image for each unit time is the urine region may be estimated by comparing the total sum of a plurality of connecting lines with a preset value.

The artificial neural network 800 of the MLP model learns by adjusting the learning parameters. According to one embodiment, the learning parameters include at least one of a weight and a deviation. The learning parameters are iteratively adjusted through an optimization algorithm called gradient descent. Whenever an estimation result is calculated from a given data sample (forward propagation), performance of the network is evaluated through a loss function that measures an estimation error. Each learning parameter of the artificial neural network 800 is adjusted by slightly increasing in a direction to minimize the value of the loss function, and this process is referred to as backpropagation.

Through the above model, the urine region may be separated from the ultrasonic image of the bladder.

In addition, in the same way, it is possible to separate the regions of the outer wall of the bladder and the detrusor muscle in the bladder from the ultrasonic image of the bladder.

FIG. 9 illustrates a process of calculating a three-dimensional urine volume from a two-dimensional ultrasonic image according to various embodiments of the present disclosure.

Referring to FIG. 9, two spheres for radii r1 and r2 correspond to a sphere for the entire volume of the bladder and a sphere for the volume of the urine region 910. A difference of r1−r2 corresponds to the detrusor muscle 930 in the bladder. Therefore, a difference between the volume of the sphere of radius r1 and the volume of the sphere of radius r2 corresponds to a volume of the detrusor muscle 930.

Since the bladder increases or decreases in volume like a water balloon according to the amount of urine, the volume thereof may be calculated by assuming the bladder to be one sphere.

To date, there is no instrument capable of monitoring a change in bladder volume in real time. There are two currently used devices and methods for the volume of urine or bladder. First, measuring the flow rate discharged from the bladder in real time is the uroflowmetry of FIG. 2. Second, measuring residual urine in the bladder using ultrasound is the bladder sono scan in FIG. 3.

The present disclosure provides a method and apparatus for unifying the uroflowmetry and bladder sono scan by calculating the amount of urine output in real time based on a cross-sectional area of the bladder using ultrasound.

What can be obtained through ultrasound imaging is a two-dimensional image, but when the volume of the sphere is calculated by assuming the urine region of black shade confirmed from the two-dimensional image to be a sphere, a three-dimensional estimated urine volume may be calculated.

Since the urine region does not have a shape of a perfect circle, the estimated urine volume can be calculated by calculating a radius of a circle having the same area as the urine region and then calculating a volume of a sphere having the calculated radius. That is, when the area of the urine region is represented by S, a radius r of a circle having the same area as the urine region may be calculated through Equation $S=\pi r^2$. In addition, it is possible to calculate the estimated urine volume V by calculating the volume of the sphere having the radius r calculated through Equation $V=(4/3)\pi r^3$.

The change amount for each unit time of the estimated urine volume V calculated by for each unit time is the urinary flow rate for each unit time that may be confirmed in the uroflowmetry of FIG. 2. That is, the urinary flow rate for each unit time is a differential value for the unit time of at least one estimated urine volume for each unit time.

In addition, when the urination ends, that is, the estimated urine volume calculated at the time when the change in the estimated urine volume calculated by for each unit time stops, is the residual urine volume that can be confirmed in the bladder sono scan of FIG. 3.

Therefore, according to the method and apparatus for diagnosing the urinary disturbances according to various embodiments of the present disclosure, it is possible to measure the urinary flow rate for each unit time and the residual urine volume at the same time.

FIG. 10 illustrates a graph of the urinary flow rate and the amount of urine measured by the method for diagnosing the urinary disturbances according to various embodiments of the present disclosure.

FIG. 11 illustrates a graph of the urinary flow rate measured by the method of the uroflowmetry of FIG. 2.

Specifically, FIG. 10 illustrates a line showing the urinary flow rate for each unit time calculated by differentiating the calculated estimated urine volume for each unit time with respect to each unit time and a line showing the amount of urine for each unit time calculated by integrating the urinary flow rate for each unit time with respect to the unit time after modeling the bladder in three dimensions assuming the bladder to be a spherical shape from the two-dimensional ultrasonic image. In FIG. 10, a line increasing from zero and decreasing and converging back to zero is the line showing the urinary flow rate, and a line increasing from zero and not decreasing is the line showing the amount of urine. In addition, FIG. 11 is a graph of urinary flow rate measured by the method of the uroflowmetry of FIG. 2 for the same patient as in FIG. 10.

The graph of the urinary flow rate of FIG. 10 is the graph of the urinary flow rate measured for the entire urination process. A horizontal axis of the graph of the urinary flow rate of FIG. 10 represents time (minutes:seconds). A horizontal axis of the graph of the urinary flow rate of FIG. 11 represents time in units of $1/1000$ seconds, and an origin of the graph of the urinary flow rate of FIG. 11 is a time point (1 minute:00 seconds) on the horizontal axis of the graph of the urinary flow rate of FIG. 10.

When the graph of the urinary flow rate of FIG. 10 and the graph of the urinary flow rate of FIG. 11 are compared with each other, a similar graph form is illustrated with respect to the change in the urinary flow rate. In particular, in the graph of the urinary flow rate of FIG. 10 and the graph of the urinary flow rate of FIG. 11, while the urinary flow rate is decreasing, the urinary flow rate briefly rebounds and then decreases again, and the urinary flow rate converges to zero and then converges to zero again after rebounding.

The clinician can determine presence of an obstruction in the urinary tract from whether the graph of the urinary flow rate has a normal shape. Therefore, the clinician can make the same determination as to whether the obstruction exists in the urinary tract from the graph of the urinary flow rate of FIG. 10 and the graph of the urinary flow rate of FIG. 11.

In addition, in the measurement of the residual urine volume, for an error between the residual urine volume measured according to various embodiments of the present disclosure and the residual urine volume measured by the method of the bladder sono scan of FIG. 3 for the same patient, only a slight difference of 1 cc on average is confirmed for six patients.

Through experimentation, feasibility and industrial applicability of an apparatus and method that can measure the urinary flow rate and the residual urine simultaneously by unifying the uroflowmetry and bladder sono scan, which are used for measurement of objective urinary disorder test index for patients complaining of the urinary disturbances were confirmed.

When implementing the embodiments of the present disclosure using hardware, application specific integrated circuits (ASICs), digital signal processors (DSPs), digital signal processing devices (DSPDS), programmable logic devices (PLDs), field programmable gate arrays (FPGAs), or the like for carrying out the present disclosure may be provided in the processor 505 of the present disclosure.

Meanwhile, the above-described method can be written as a program that can be executed on a computer and can be implemented in a general-purpose digital computer that operates the program using a computer-readable medium. In addition, the structure of the data used in the above-described method may be stored in a computer-readable storage medium through various means. Program storage devices that may be used to describe a storage device including executable computer code for performing the various methods of the present disclosure should not be construed as including transitory objects such as carrier waves or signals. The computer-readable storage medium includes a storage medium such as a magnetic storage medium (that is, read only memory (ROM), floppy disk, hard disk, or the like) and an optically readable medium (that is, compact disk (CD)-ROM, digital versatile disk (DVD), or the like).

The embodiments described above are those in which components and features of the present disclosure are combined in a predetermined form. Each component or feature should be considered to be optional unless explicitly stated otherwise. Each component or feature may be implemented in a form that is not combined with other components or features. In addition, it is also possible to configure an embodiment of the present disclosure by combining some components and/or features. The order of operations described in the embodiments of the disclosure may be changed. Some configurations or features of an embodiment may be included in other embodiments or may be replaced with corresponding configurations or features of other embodiments. It is obvious that claims that are not explicitly cited in the claims can be combined to form an embodiment or included as a new claim by amendment after filing.

It will be apparent to those skilled in the art that the present disclosure can be embodied in other forms without departing from the spirit and essential characteristics of the present disclosure. Accordingly, the above embodiments should be considered in all respects as illustrative and not restrictive. The scope of the present disclosure should be determined by a reasonable interpretation of the appended claims and all possible changes within the equivalent scope of the present disclosure.

The present disclosure can provide a method and apparatus for diagnosing urinary disturbances by simultaneously measuring a urinary flow rate and residual urine. Specifically, the present disclosure can provide a method and apparatus for diagnosing urinary disturbances by measuring a volume and a change in the volume of a urine region in a three-dimensional bladder using a two-dimensional ultrasonic image obtained for each unit time while a patient is urinating to simultaneously perform uroflowmetry and bladder sono scan.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

In this application, the term "controller" and/or "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components (e.g., op amp circuit integrator as part of the heat flux data module) that provide the described functionality; or a combination of some or all of the above, such as in a system-on-chip.

The term memory is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A method performed by an apparatus for diagnosing urinary disturbances, wherein the apparatus comprises an input device configured to obtain at least one ultrasonic image for a unit time for a bladder from a patient who is urinating, a memory configured to store the at least one ultrasonic image for the unit time, an output device configured to display information, and at least one processor operably coupled to the input device, the memory, and the output device, wherein the method comprises:

obtaining, by the input device, a plurality of ultrasonic images of the bladder for the unit time from the patient while the patient is urinating, wherein the input device is fixedly positioned at the patient's lower abdomen while the patient is urinating, and the unit time can be configured based on an average urination time of the patient;

obtaining, by the at least one processor, a plurality of urine region images for the unit time from the plurality of ultrasonic images for the unit time;

calculating, by the at least one processor, a plurality of estimated urine volumes for the unit time based on areas of the plurality of urine region images for the unit time;

calculating, by the at least one processor, at least one parameter value with respect to urinary disturbances based on the plurality of estimated urine volumes for the unit time; and outputting, by the output device, the at least one parameter value, wherein the at least one parameter includes a residual urine volume and a urinary flow rate for the unit time, wherein a value of the residual urine volume is a value of one of the plurality of estimated urine volumes which is calculated at a time when a change in the plurality of estimated urine volumes for the unit time stops, wherein the urinary flow rate for the unit time is a differential value for the unit time of the plurality of estimated urine volumes for the unit time.

2. The method of claim 1, wherein the calculating of the plurality of estimated urine volumes for the unit time includes:

calculating radii of circles having same areas as areas of the plurality of urine region images for the unit time; and calculating the plurality of estimated urine volumes for the unit time as volumes of spheres having the radii.

3. The method of claim 1, wherein the obtaining of the plurality of urine region images for the unit time includes:

separating an outer wall region, a detrusor muscle region, and a urine region of the bladder from each of the plurality of ultrasonic images for the unit time; and obtaining each of the plurality of urine region image for the unit time as the urine region.

4. The method of claim 1, wherein the at least one parameter further includes at least one of a time taken to empty the bladder, and an amount of urine.

5. The method of claim 4, wherein the time taken to empty the bladder is a length of a time interval from a time when the plurality of estimated urine volumes for the unit time start to change to a time when a change in the plurality of estimated urine volumes for the unit time stops.

6. The method of claim 4, wherein a value of the amount of urine is a difference between another one of the plurality of estimated urine volumes which is calculated at a time when the plurality of estimated urine volumes for the unit time start to change and the one of the plurality of estimated urine volumes which is calculated at a time when the change in the plurality of estimated urine volumes for the unit time stops.

7. The method of claim 1, wherein the obtaining of the plurality of ultrasonic region images for the unit time is performed using a urine region separation model stored in a memory.

8. The method of claim 7, wherein the urine region separation model includes an input layer, a plurality of hidden layers, and an output layer, and
the obtaining of the plurality of urine region images for the unit time includes:
inputting a red-green-blue (RGB) value of each pixel in the plurality of ultrasonic images for the unit time to the input layer;
connecting units defined as a plurality of nodes stored in each of the plurality of hidden layers to the RGB value of each pixel in the plurality of ultrasonic images for the unit time;
generating an estimated value for whether or not the urine region is present in each pixel in the plurality of ultrasonic images for the unit time based on a correlation between the RGB value of each pixel in the plurality of ultrasonic images for the unit time and the units; and
obtaining the plurality of urine region images for the unit time as each pixel in the plurality of ultrasonic images for the unit time when the estimated value is equal to or more than a predetermined threshold value.

9. An apparatus for diagnosing urinary disturbances, the apparatus comprising:
an input device configured to be fixedly positioned at a lower abdomen of a patient while the patient is urinating and to obtain at least one ultrasonic image for a unit time for a bladder from the patient who is urinating;
a memory configured to store the at least one ultrasonic image for the unit time;
an output device configured to display information; and
at least one processor operably coupled to the input device, the memory, and the output device,
wherein the at least one processor is configured to:
obtain, by the input device, a plurality of ultrasonic images of the bladder for the unit time from the patient while the patient is urinating;
obtain, by the at least one processor, a plurality of urine region images for the unit time from the plurality of ultrasonic images for the unit time;
calculate, by the at least one processor, a plurality of estimated urine volumes for the unit time based on areas of the plurality of urine region images for the unit time;
calculate, by the at least one processor, at least one parameter value with respect to urinary disturbances based on the plurality of estimated urine volumes for the unit time; and
output, by the output device, the at least one parameter value,
wherein the at least one parameter includes a residual urine volume and a urinary flow rate for the unit time,
wherein a value of the residual urine volume is a value of one of the plurality of estimated urine volumes which is calculated at a time when a change in the plurality of estimated urine volumes for the unit time stops,
wherein the urinary flow rate for the unit time is a differential value for the unit time of the plurality of estimated urine volumes for the unit time.

* * * * *